(12) United States Patent
Nitta et al.

(10) Patent No.: US 11,464,927 B2
(45) Date of Patent: Oct. 11, 2022

(54) RESPIRATORY ASSISTANCE DEVICE

(71) Applicant: Metran Co., Ltd., Kawaguchi (JP)

(72) Inventors: Kazufuku Nitta, Saitama (JP); Shinichi Shiota, Saitama (JP)

(73) Assignee: Metran Co., Ltd., Kawaguchi (JP)

(*) Notice: Subject to any disclaimer, the term of this patent is extended or adjusted under 35 U.S.C. 154(b) by 424 days.

(21) Appl. No.: 15/766,637

(22) PCT Filed: Sep. 16, 2016

(86) PCT No.: PCT/JP2016/077359
§ 371 (c)(1),
(2) Date: Apr. 6, 2018

(87) PCT Pub. No.: WO2017/064973
PCT Pub. Date: Apr. 20, 2017

(65) Prior Publication Data
US 2018/0296780 A1    Oct. 18, 2018

(30) Foreign Application Priority Data

Oct. 16, 2015 (JP) .............................. JP2015-205053

(51) Int. Cl.
*A61M 16/00* (2006.01)
*A61M 16/16* (2006.01)
*A61M 16/10* (2006.01)

(52) U.S. Cl.
CPC .... *A61M 16/0066* (2013.01); *A61M 16/0003* (2014.02); *A61M 16/026* (2017.08);
(Continued)

(58) Field of Classification Search
CPC .............. A61M 16/00; A61M 16/0003; A61M 16/021; A61M 16/202; A61M 16/203;
(Continued)

(56) References Cited

U.S. PATENT DOCUMENTS 7,574,368 B2    8/2009  Pawlikowski et al.
8,146,590 B2    4/2012  Nitta
(Continued)

FOREIGN PATENT DOCUMENTS

JP    2004-516562 A    6/2004
JP    2006-223332 A    8/2006
(Continued)

OTHER PUBLICATIONS

Anthropometric Data obtained from https://multisite.eos.ncsu.edu/www-ergocenter-ncsu-edu/wp-content/uploads/sites/18/2016/06/Anthropometric-Detailed-Data-Tables.pdf (Year: 2006).*
(Continued)

*Primary Examiner* — Valerie L Woodward
*Assistant Examiner* — Paige Kathleen Bugg
(74) *Attorney, Agent, or Firm* — Flynn Thiel, P.C.

(57) ABSTRACT

Respiratory assistance device suitable for Auto CPAP respiratory therapy. The respiratory assistance device includes: a blower device including a blower configured to generate pressurized air; an operation device including an operation interface configured to control the blower; a wireless or wired communication arrangement configured to connect the blower device and the operation device; an attachment part configured to be attached to a head of a patient so as to supply the pressurized air to an airway of the patient; and an air tube through which the pressurized air is introduced into the attachment part from the blower device. The blower device is accommodated in a blower device casing, and the operation device is accommodated in an operation device casing separate from the blower device casing.

9 Claims, 10 Drawing Sheets

(52) U.S. Cl.
CPC ............ *A61M 16/10* (2013.01); *A61M 16/16* (2013.01); *A61M 2016/003* (2013.01); *A61M 2016/0027* (2013.01); *A61M 2205/3337* (2013.01); *A61M 2205/3368* (2013.01); *A61M 2205/3584* (2013.01); *A61M 2205/3653* (2013.01); *A61M 2205/42* (2013.01); *A61M 2205/505* (2013.01); *A61M 2205/8262* (2013.01)

(58) Field of Classification Search
CPC ............ A61M 16/204; A61M 16/205; A61M 16/022; A61M 16/0875; A61M 16/10; A61M 16/16; A61M 16/026; A61M 2016/0027; A61M 2016/003; A61M 2205/3337; A61M 2205/3368; A61M 2205/3584; A61M 2205/3653; A61M 2205/42; A61M 2205/505; A61M 2205/8262
See application file for complete search history.

(56) References Cited

U.S. PATENT DOCUMENTS

| | | | | |
|---|---|---|---|---|
| 2006/0237013 | A1* | 10/2006 | Kwok | A61M 16/0605 128/204.23 |
| 2007/0045152 | A1* | 3/2007 | Kwok | A61M 16/00 206/733 |
| 2007/0193582 | A1* | 8/2007 | Kwok | A61M 16/0069 128/204.18 |
| 2009/0126735 | A1* | 5/2009 | Nitta | A61M 16/1075 128/203.26 |
| 2009/0320842 | A1* | 12/2009 | Doherty | A61M 16/0066 128/204.21 |
| 2010/0132708 | A1* | 6/2010 | Martin | A61M 16/0066 128/204.17 |
| 2012/0120635 | A1* | 5/2012 | Strong | F21V 5/008 362/105 |
| 2012/0145155 | A1* | 6/2012 | Peake | A61M 16/0816 128/205.12 |
| 2013/0306072 | A1 | 11/2013 | Moir et al. | |
| 2014/0109910 | A1 | 4/2014 | Colbaugh | |
| 2015/0157818 | A1 | 6/2015 | Darby et al. | |
| 2015/0231349 | A1 | 8/2015 | Ahmad et al. | |
| 2015/0320954 | A1* | 11/2015 | Suzuki | A61M 16/0066 128/204.21 |
| 2016/0015926 | A1* | 1/2016 | Hermez | A61M 16/06 128/203.26 |
| 2016/0339201 | A1 | 11/2016 | Nitta | |
| 2017/0211438 | A1* | 7/2017 | Suzuki | F01N 1/08 |
| 2017/0216552 | A1* | 8/2017 | Goff | A61M 16/0816 |
| 2018/0085544 | A1* | 3/2018 | Holyoake | A61M 16/024 |

FOREIGN PATENT DOCUMENTS

| | | | |
|---|---|---|---|
| JP | 2014-508594 A | | 4/2014 |
| JP | 2014-83373 A | | 5/2014 |
| JP | 2014-117445 A | | 6/2014 |
| JP | 2014117445 A | * | 6/2014 |
| JP | 2014-526280 A | | 10/2014 |
| JP | 2015-142646 A | | 8/2015 |

OTHER PUBLICATIONS

International Search Report issued in PCT/JP2016/077359 dated Dec. 20, 2016 with English translation (5 pages).
Written Opinion issued in PCT/JP2016/077359 dated Dec. 20, 2016 (5 pages).
European Search Report issued in Application No. 16855227.1, dated Aug. 6, 2018 (4 pp.).

* cited by examiner

[Figure 1]
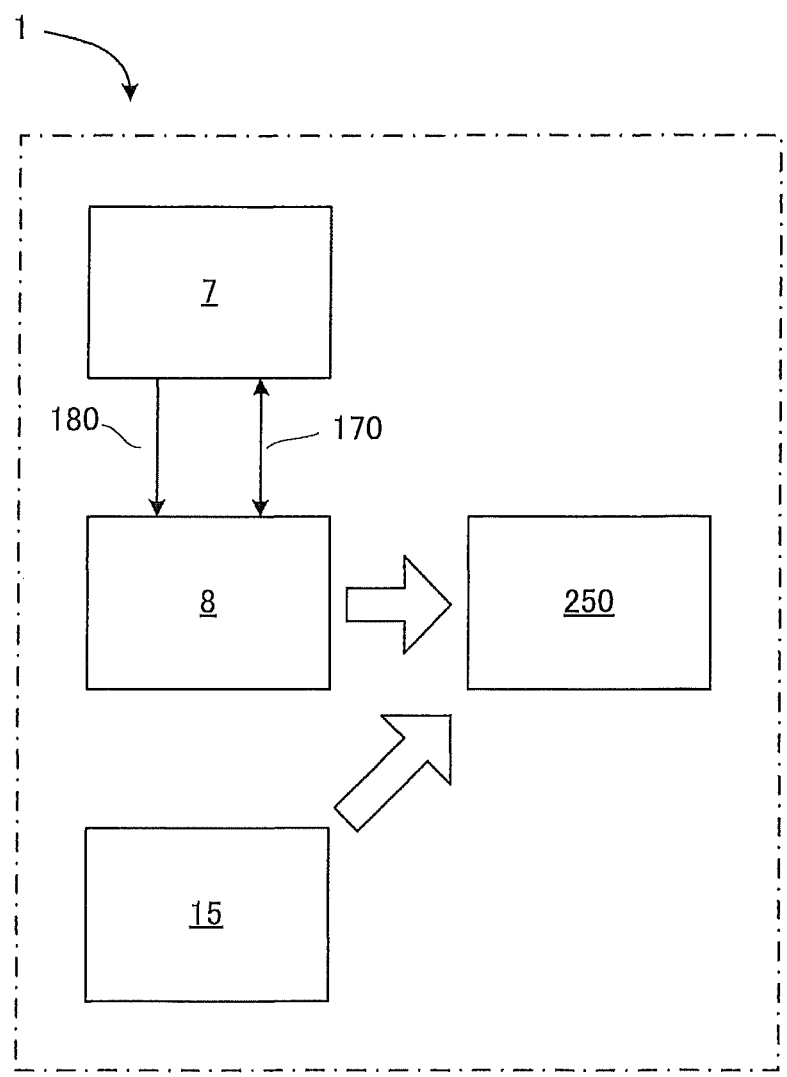

[Figure 2]
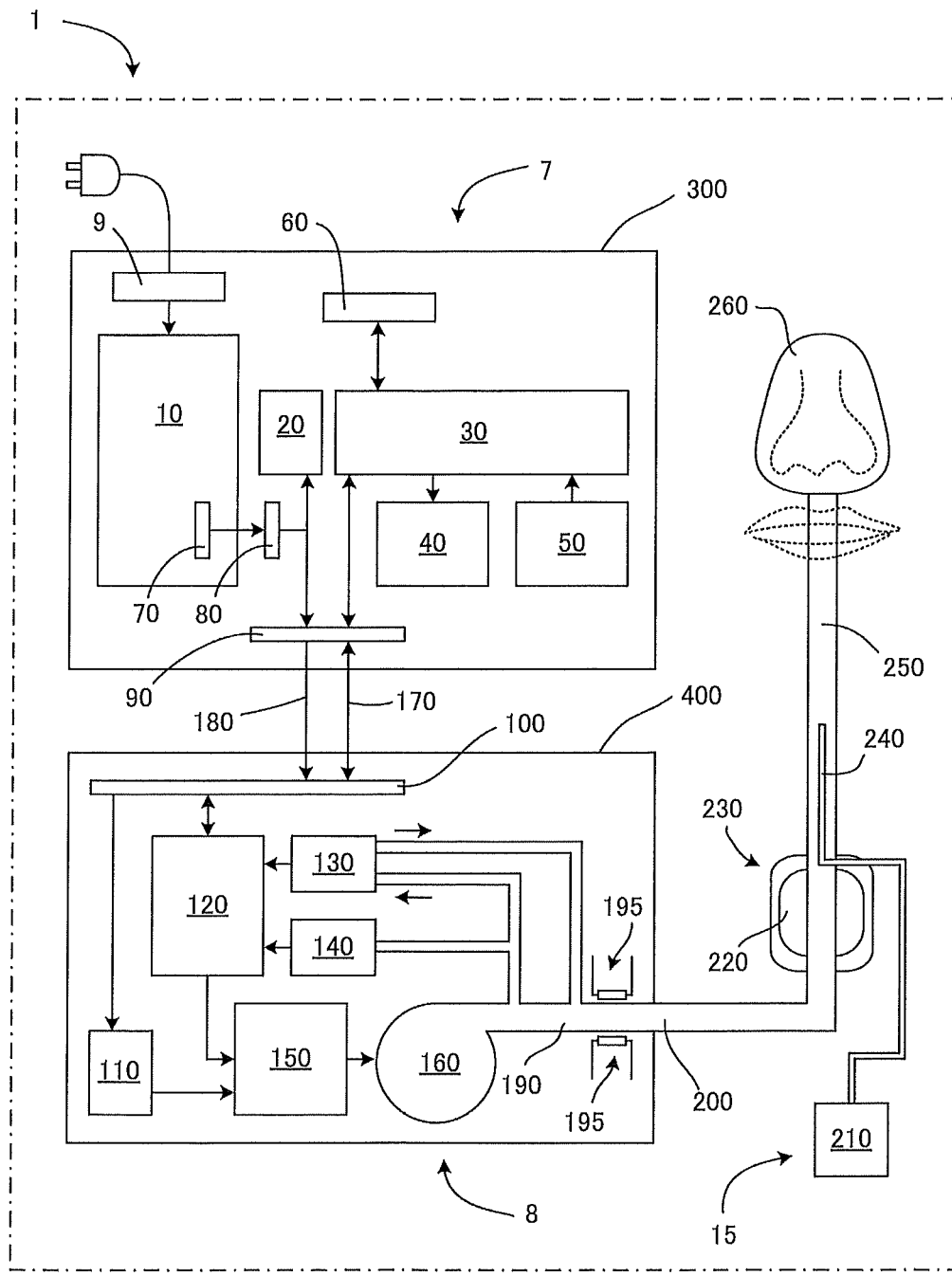

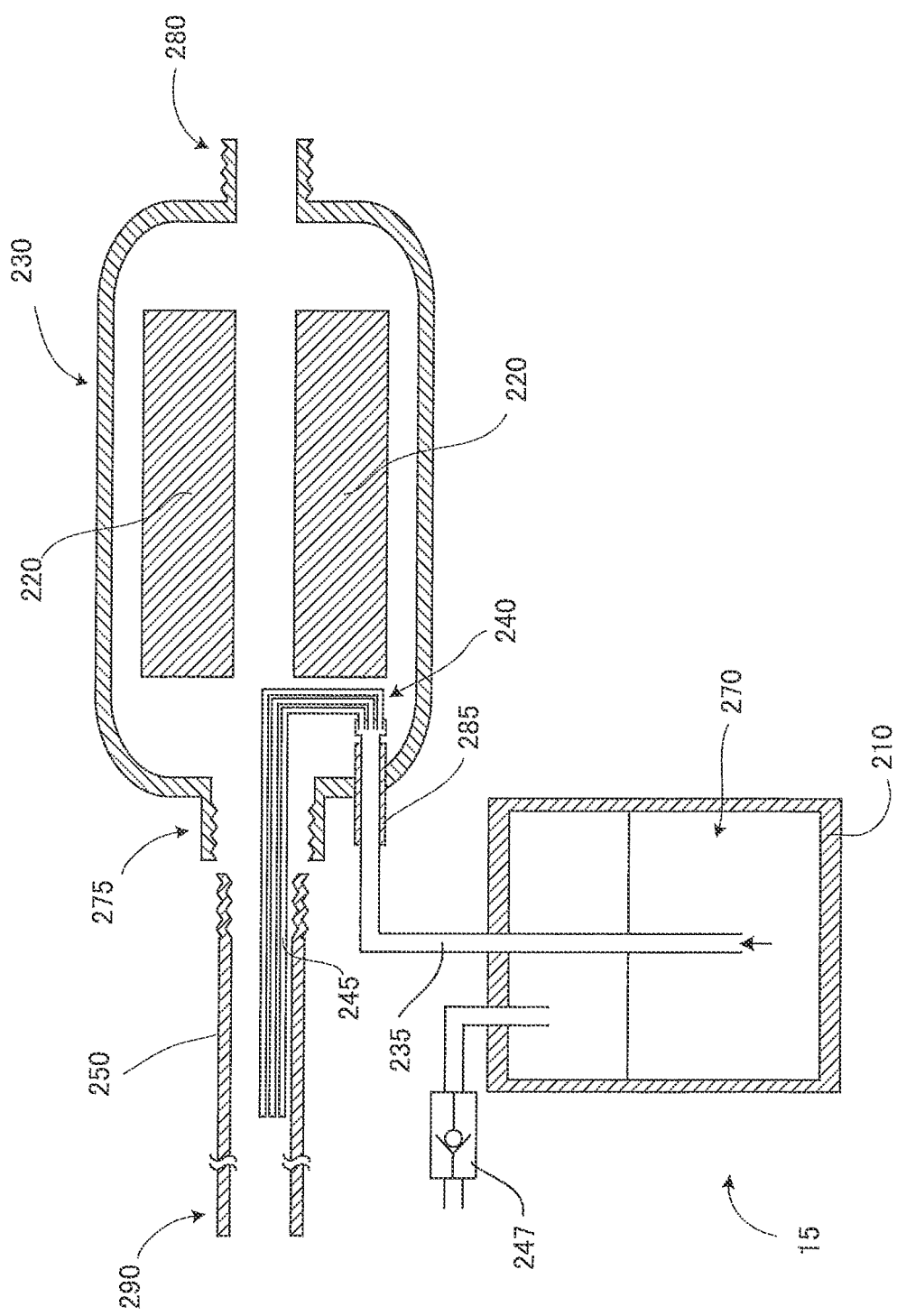
[Figure 3]

[Figure 4]
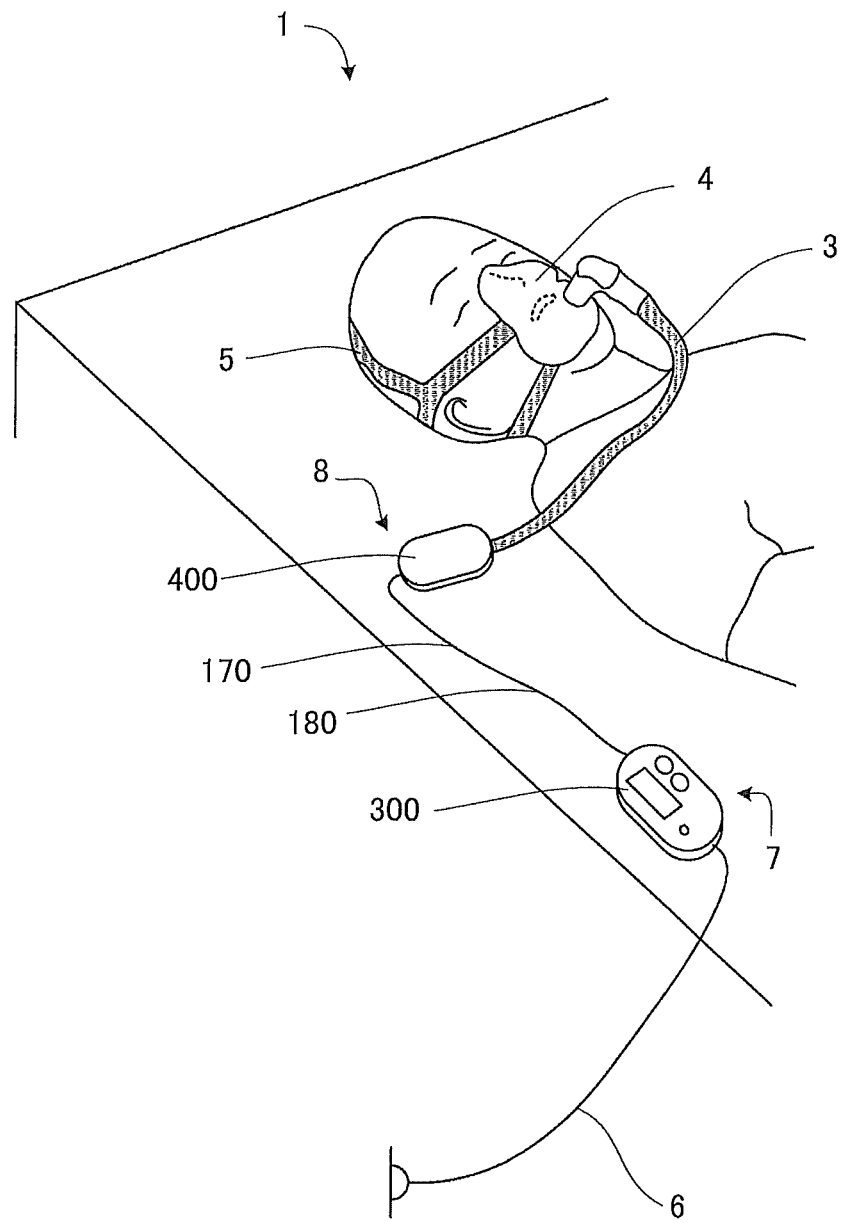

[Figure 5]
(a)
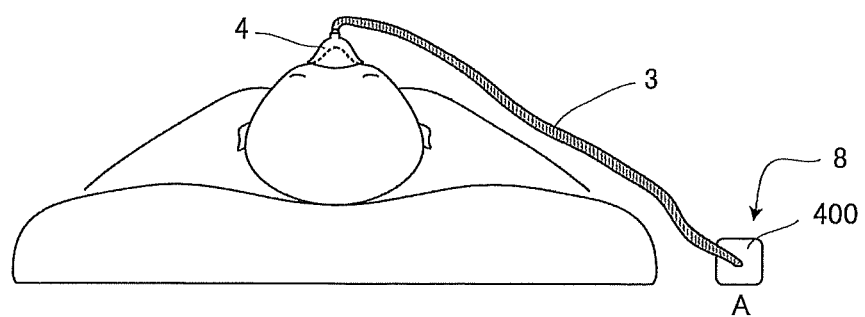
(b)
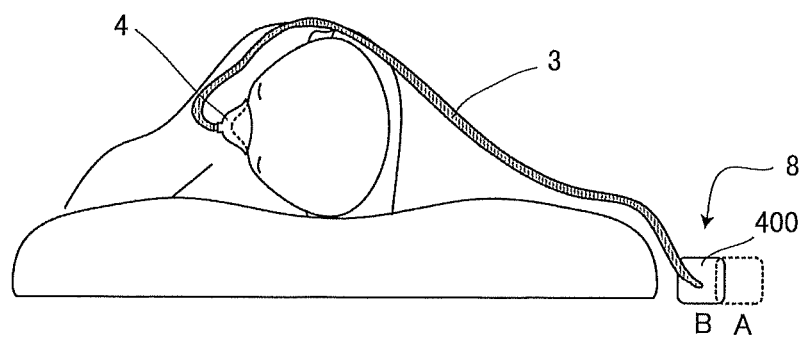
(c)
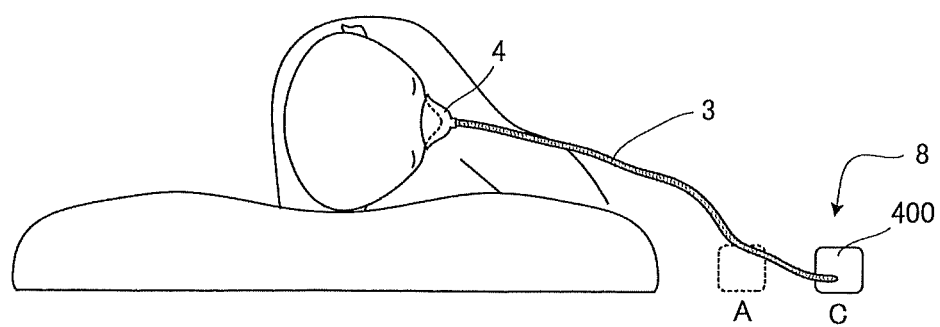

[Figure 6]
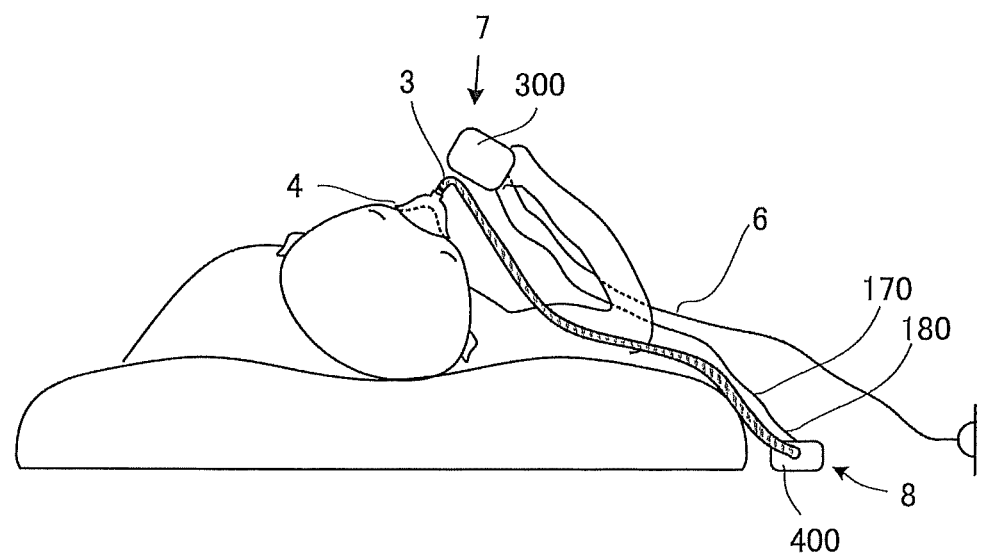

[Figure 7]
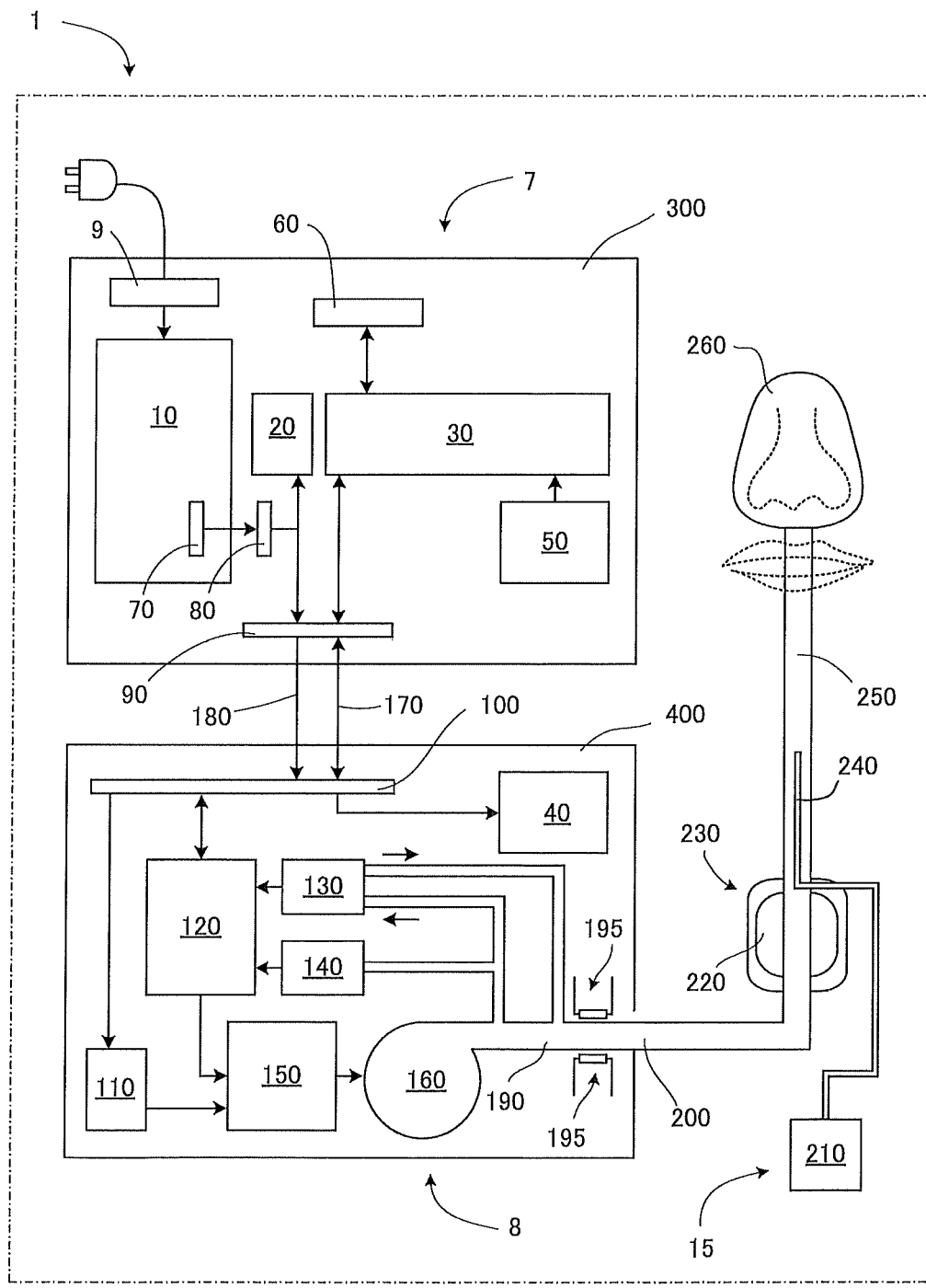

[Figure 8]
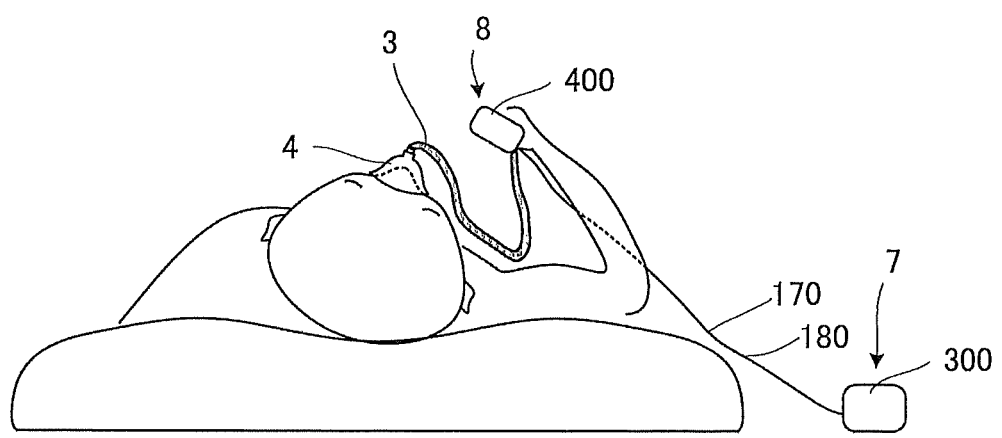

[Figure 9]
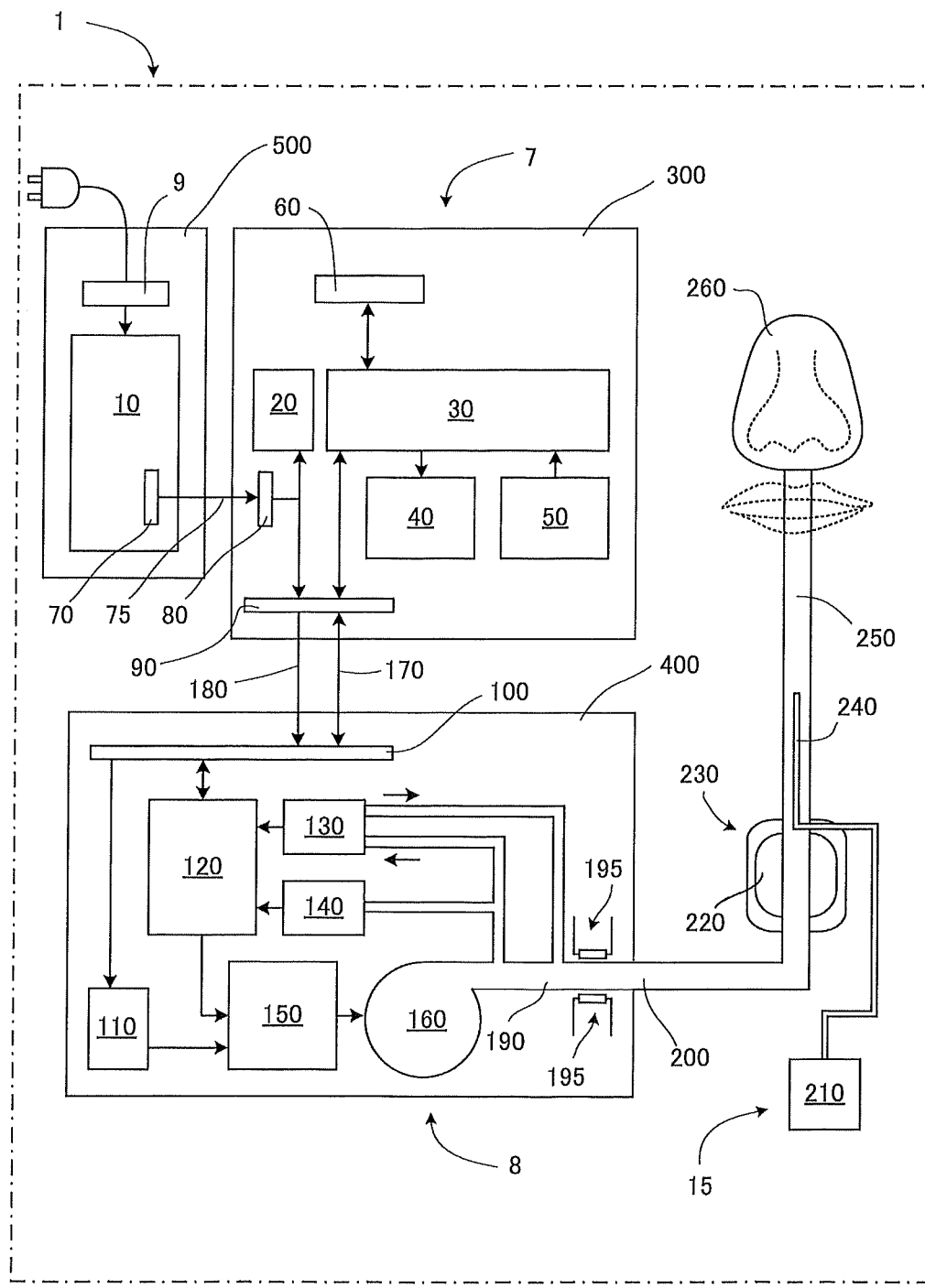

[Figure 10]
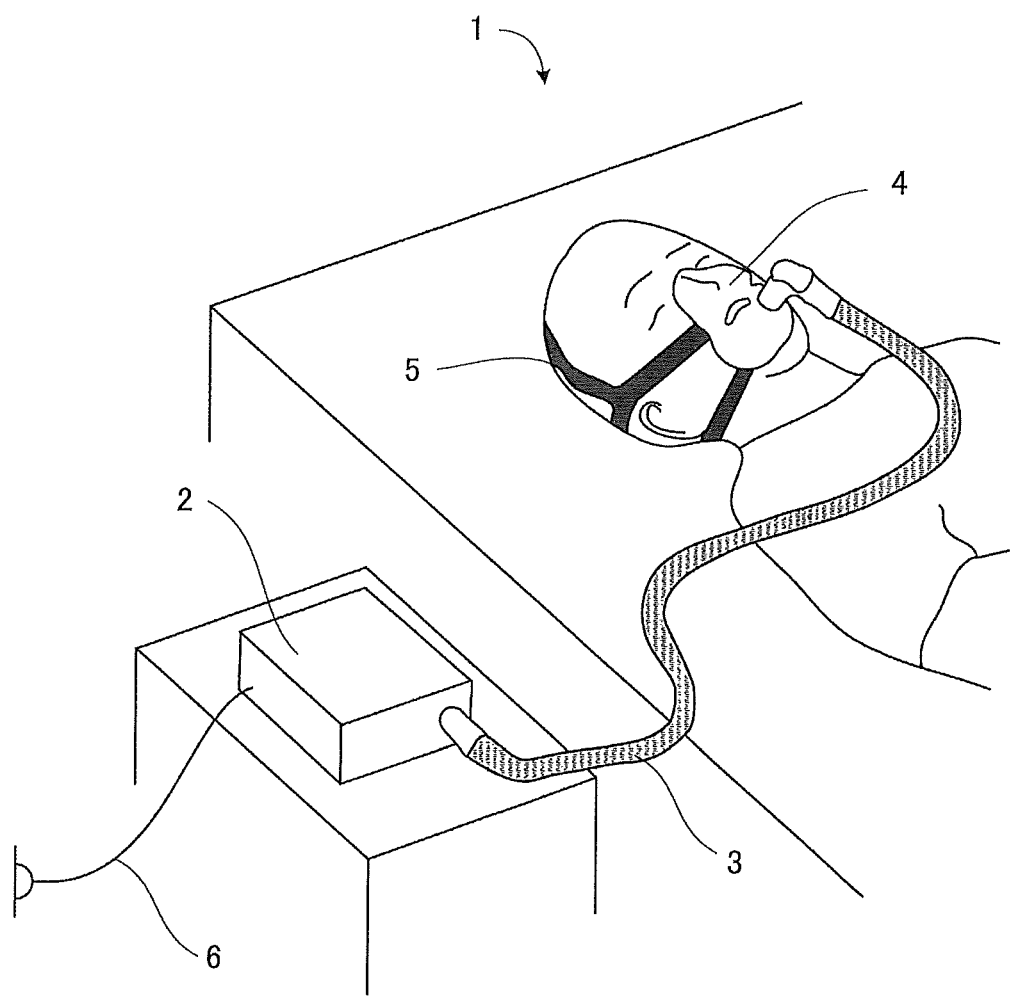

RESPIRATORY ASSISTANCE DEVICE

TECHNICAL FIELD

The present invention relates to a respiratory assistance device suitable for therapy equipment or the like for automatic continuous positive airway pressure respiratory therapy.

BACKGROUND ART

Sleep Apnea Syndrome (SAS) occurs in such a manner that muscles of the airway relax during sleep so that the root of the tongue or the soft palate lowers thus obstructing the airway. It is said that the number of potential SAS patients in Japan is more than three million. The risk of occurrence of circulatory system disease for an SAS patient is considered two to four times higher than for a healthy person. Further, an SAS patient has a high possibility of having sleeping disorders which cause the patient to exhibit symptoms of severe drowsiness and hence, the risk of occurrence of a traffic accident for an SAS patient is two or more times higher than for a healthy person. It is considered effective for a patient suffering from SAS to receive Auto CPAP respiratory therapy (CPAP therapy) which utilizes a respiratory assistance device including a blower which applies a positive pressure to the airway (see Japanese Patent Laid-Open No. 2015-142646, and Metran Co., Ltd., [online], product information>Jusmine, [retrieved on Sep. 16, 2015], Internet (URL: http://www.metran.co.jp/products/products2/190.html), for example). Such a respiratory assistance device uses compressed air supplied from the blower as intake air, and supplies the pressurized air to the airway of a patient.

Conventionally, a respiratory assistance device is formed of a body device part which is an integral body of an operation device and a blower device, an attachment part which is attached to a patient, and an artificial ventilator breathing circuit (air tube) which connects the body device part and the attachment part with each other. When air is continuously supplied by the blower during sleep time, the nasal cavity and the oral cavity are dried out thus not only causing the patient to feel extreme discomfort but also causing symptoms where the patient has a sore throat or has difficulty in projecting his/her voice. To alleviate such symptoms, a heating and humidifying device is provided to the respiratory assistance device in many cases. The heating and humidifying device is generally formed of a water storage part and a heating and humidifying part for evaporating water. The heating and humidifying device applies moisture to pressurized air so as to reduce the above-mentioned feeling of discomfort.

SUMMARY OF INVENTION

Technical Problem

First, FIG. 10 shows a usage mode and a drawback of the conventional respiratory assistance device. Thereafter, tasks to be solved by the present invention are described. As shown in FIG. 10, in the conventional respiratory assistance device 1, an attachment part 4 which supplies air (pressurized air) of a positive pressure to the airway is attached so as to cover the nose and the mouth (there may be a case where the attachment part 4 covers only the nose). Usually, during the operation of CPAP (Continuous Positive Airway Pressure respiratory therapy), a positive pressure of approximately 4.0 to 20.0 cm H2O is applied. Accordingly, the attachment part 4 is fixed to the head by an attachment part fixture 5 so as to prevent the attachment part 4 from displacing from the head during sleep.

The attachment part 4 is joined to an air tube 3, and the air tube 3 is connected to the body device 2 which incorporates the blower. The body device 2 must be constantly driven during sleep time. Accordingly, electric power is supplied to the body device 2 from a general household outlet through an AC power source line 6. Therefore, an AC adapter must be attached to the body device which is an integral body of the blower, the operation device performing control of an entire apparatus and the like. Further, when the above-mentioned heating and humidifying device (having a size substantially equal to the size of the body device) is connected to the body device 2, the total weight of the AC adapter with a larger capacity and the body device becomes 2 to 3 Kg in many cases.

The air tube 3 which connects the body device 2 and the attachment part 4 supplies air of a positive pressure necessary for performing a treatment. Accordingly, a material which is strong and relatively heavy is uses for forming the air tube 3. In addition, the respiratory assistance device is used during sleep and hence, it is necessary for the respiratory assistance device to reduce noises from the blower as much as possible. For this reason, the length of the air tube becomes approximately 2 m in many cases so as to increase a distance between the blower and the attachment part. This also becomes a cause of an increase in weight of the entire air tube. The body device 2 has a weight of 1 to 2 Kg. Accordingly, in the case where the air tube 3 has a short length, when a patient wears the attachment part, the degree of freedom of the head is restricted so that the patient cannot easily roll over during sleep. Therefore, the attachment part itself becomes a cause of sleep disturbance. Further, portability is also reduced.

The present invention has been made under such circumstances, and it is an object of the present invention to provide a respiratory assistance device which has a small size and light weight, can be easily handled, has a favorable portability, and can contribute to the enhancement of quality of life (QOL) of a patient.

Solution to Problem (1) The present invention provides a respiratory assistance device which includes: a blower device including a blower configured to generate pressurized air; an operation device including an operation interface configured to control the blower; wireless or wired communication means configured to connect the blower device and the operation device to each other; an attachment part configured to be attached to a head of a patient so as to supply the pressurized air to an airway of the patient; and an air tube through which the pressurized air is introduced into the attachment part from the blower device, wherein the blower device is accommodated in a blower device casing, and the operation device is accommodated in an operation device casing separate from the blower device casing.

(2) The present invention also provides the respiratory assistance device described in the above-mentioned (1), and characterized by further including: a power source unit accommodated in the operation device casing, and configured to supply electric power to the blower and the operation interface; and an electric power distribution line configured to distribute the electric power from the power source unit to the blower device casing.

(3) The present invention also provides the respiratory assistance device described in the above-mentioned (2), and characterized in that a length of the electric power distribution line is set to 50 cm or more.

(4) The present invention also provides the respiratory assistance device described in any one of the above-mentioned (1) to (3), and characterized by further including a control unit disposed in the operation device casing, and configured to perform at least part of control of the blower.

(5) The present invention also provides the respiratory assistance device described in any one of the above-mentioned (1) to (4), and characterized by further including a measuring part configured to detect a flow rate or a pressure of the pressurized air.

(6) The present invention also provides the respiratory assistance device described in the above-mentioned (5), and characterized in that a signal of the measuring part is transmitted to the control unit through the communication means.

(7) The present invention also provides the respiratory assistance device described in any one of the above-mentioned (1) to (6), and characterized in that a length of the air tube is set to 30 cm or more.

(8) The present invention also provides the respiratory assistance device described in any one of the above-mentioned (1) to (7), and characterized in that a length of the air tube is set to 1 m or less.

(9) The present invention also provides the respiratory assistance device described in any one of the above-mentioned (1) to (8), and characterized by further including a humidifier configured to provide moisture to the pressurized air.

(10) The present invention also provides the respiratory assistance device described in the above-mentioned (9), and characterized in that the humidifier includes: a water storage part configured to contain water for humidification; and a humidifying part disposed in the air tube, and configured to humidify the pressurized air with water in the water storage part.

(11) The present invention also provides the respiratory assistance device described in the above-mentioned (10), and characterized in that the humidifier further includes a pressure applying part configured to pressurize water in the water storage part by an elastic member.

(12) The present invention also provides the respiratory assistance device described in any one of the above-mentioned (1) to (11), and characterized by further including a soundproofing device disposed at an intermediate portion of a flow passage for the pressurized air, and configured to absorb sound of the blower.

(13) The present invention also provides the respiratory assistance device described in the above-mentioned (12), and characterized in that the soundproofing device includes: a humidifier connection portion connected to the humidifier; a body-side connection portion connected to a breathing circuit connection port; an air-tube-side connection portion connected to the air tube; and a sound absorbing member disposed between the body-side connection portion and the air-tube-side connection portion.

(14) The present invention also provides the respiratory assistance device described in any one of the above-mentioned (1) to (13), and characterized by further including a heating part capable of heating the pressurized air to a predetermined temperature.

Advantageous Effect of Invention

According to the respiratory assistance device described herein, it is possible to acquire an advantageous effect of providing therapy equipment for a continuous positive airway pressure respiratory therapy which has a small size and light weight, can be easily handled, and has a favorable portability.

BRIEF DESCRIPTION OF DRAWINGS

FIG. 1 is an overall configuration diagram of a respiratory assistance device according to an embodiment of the present invention.

FIG. 2 is a detailed block diagram of the respiratory assistance device according to a first embodiment of the present invention.

FIG. 3 is an explanatory view of a soundproofing device and a humidifier according to the first embodiment of the present invention.

FIG. 4 is a conceptual view showing a usage mode of the respiratory assistance device according to the first embodiment of the present invention.

FIG. 5 is an explanatory view showing advantageous effects of the respiratory assistance device according to the first embodiment of the present invention.

FIG. 6 is an explanatory view showing advantageous effects of the respiratory assistance device according to the first embodiment of the present invention.

FIG. 7 is a detailed block diagram of a respiratory assistance device according to a second embodiment of the present invention.

FIG. 8 is an explanatory view showing advantageous effects of the respiratory assistance device according to the second embodiment of the present invention.

FIG. 9 is a detailed block diagram of a respiratory assistance device according to a third embodiment of the present invention.

FIG. 10 is a conceptual view showing a usage mode of a conventional respiratory assistance device.

DESCRIPTION OF EMBODIMENTS

Hereinafter, embodiments of the present invention are described with reference to attached drawings. FIG. 1 to FIG. 9 show only one example of a mode for carrying out the invention. In the drawings, parts given the same numerals indicate identical parts.

In the first embodiment of the present invention, an operation device (including a power source unit, a control unit which performs control of an entire apparatus, a display part, an operation interface and the like) and a blower device (including a blower, a flow rate measuring device, a pressure measuring device, a blower device control unit which controls the blower and the like) are accommodated in different casings separate from each other, and a natural evaporation type humidifier is used in combination. Accordingly, a respiratory assistance device is provided which includes a short air tube, has a small size and light weight, does not require a large power source for heating, and can enhance QOL of a patient who wears an attachment part.

FIG. 1 is an overall configuration diagram of a respiratory assistance device 1 to which the embodiment of the present invention is applied. The respiratory assistance device 1 is formed of: an operation device 7; communication means 170; an electric power distribution line 180; a blower device 8; an air tube 250; a humidifier 15; and an attachment part 4, 260. In this drawing and other drawings, sizes, shapes, thicknesses and the like of members are expressed in an exaggerated manner where necessary.

The operation device 7 and the blower device 8 are separate from each other, and are accommodated in different casings respectively. The operation device 7 and the blower device 8 are connected to each other via the communication means 170 and the electric power distribution line 180. The communication means 170 may be formed of wired communication means, which complies with existing communication standards, such as RS485. Alternatively, the communication means 170 may be formed of wireless communication means such as Bluetooth (registered trademark). Further, as described later, the blower device accommodates a blower which pressurizes air using electric power. Accordingly, the respiratory assistance device 1 includes the electric power distribution line 180 so as to supply electric power to be used for driving the blower. The length of the electric power distribution line 180 is desirably set to 50 cm or more. This is because, with such a length of the electric power distribution line 180, the blower device 8 can be placed at a distance between the face of the patient and a position within the bed, or at a distance between the face of the patient and a bedside table. This is also because such a length can increase the degree of freedom in the relative arrangement of the operation device 7 and the blower device 8. To be more specific, it may also be considered the mode where the operation device 7 is placed on a floor, and the blower device 8 is placed on a bed. Pressurized air generated by the blower device 8 is humidified by the humidifier 15 and, thereafter, is supplied to the airway of a patient from the attachment part 4 (not shown in the drawing) through the air tube 250.

FIG. 2 is a detailed block diagram of the respiratory assistance device 1 according to the first embodiment of the present invention. First, the configuration of the operation device 7 is described. The operation device 7 is accommodated in an operation device casing 300 independent from the blower device 8. The operation device 7 is formed of: a power source unit 10; a DC power circuit 20; a control unit 30; a display part 40; an operation interface 50 and the like. An AC power supplied from an AC inlet 9 is converted into a direct current (DC) by the power source unit 10. The power source unit 10 is an AC/DC converter formed of a transformer, a switching regulator and the like. Electric power converted into a DC is supplied to a DC input part 80 from a DC output part 70 which the power source unit 10 includes. Then, the electric power is distributed to the control unit 30, the display part 40, the operation interface 50, an interface 60 to a memory device and the like through the DC power circuit 20. Electric power is also supplied from the DC input part 80 to a transmission/reception interface 90, and to the blower device 8 described later through the electric power distribution line 180.

A doctor sets the respiratory assistance device 1 via the operation interface 50 so as to acquire a pressure optimum for a treatment for a patient. The doctor may perform fine adjustment of a set pressure while referring to real time measured values which are measured by a flow rate measuring device 130 and a pressure measuring device 140 described later and which are displayed on the display part 40.

The operation interface 50 is a normal push button, keyboard or switch which can be physically turned on and off. Alternatively, when the display part 40 is formed of a touch panel, the operation interface 50 is a button, a soft keyboard or the like disposed on a screen. Information inputted from the operation interface 50 is transmitted to the control unit 30.

Information stored in the memory device (not shown in the drawing) such as an SD card may also be inputted into the control unit 30 through the interface 60 to the memory device. Information stored in the memory device, such as the SD card, is setting conditions or the like for an Auto CPAP prescribed by the doctor. Measured values measured by the flow rate measuring device 130 and the pressure measuring device 140 may be recorded in the memory device such as the SD card.

The display part 40 displays various setting conditions for the Auto CPAP thereon. That is, a delay, a ramp time, a pressure setting value, actual real time measured values and the like are displayed on the display part 40.

The control unit 30 includes a CPU, a RAM, a ROM and the like for performing control of the entire respiratory assistance device 1. The central processing unit is referred to as the CPU. The CPU executes various programs thus realizing various functions. The RAM is used as a work area and a storage area for the CPU. The ROM stores an operating system and programs to be executed by the CPU. The control unit 30 desirably has a function of comparing measured values, which are measured by the flow rate measuring device 130 and the pressure measuring device 140 disposed in the blower device 8, and setting conditions and the like for the CPAP, which are inputted from the memory device through the interface 60 to the memory device, with each other so as to perform a feedback operation (a PID control or the like) thus adjusting pressure and flow rate to a fixed pressure and a fixed flow rate. At this stage of operation, the control unit 30 may transmit a command to a blower device control unit 120 described later through the communication means 170 so as to indirectly control a blower 160 thus performing at least part of control of the blower.

Next, the blower device 8 is described. The blower device 8 is accommodated in a blower device casing 400 independent from the operation device casing 300. By taking into account that the blower device casing 400 is placed on a bed or on the bedside, the blower device casing 400 preferably has a rounded design, and soft surface treatment is preferably applied to the blower device casing 400 if possible. The blower 160 includes a motor and an impeller and hence, the blower 160 generates noise, such as an operating sound and airflow noise, and vibrations. Accordingly, it is desirable for the blower device casing 400 to have sound insulation properties. The blower device 8 includes the blower device control unit 120, a blower driver 150, the blower 160, the flow rate measuring device 130, the pressure measuring device 140 and the like. The blower device 8 controls the blower 160 based on information acquired through the communication means 170 so as to compress air thus generating pressurized air. An ultrasonic flow meter may be considered for the flow rate measuring device 130. A miniaturized pressure sensor of a diaphragm-type or the like which uses an MEMS technology may be considered for the pressure measuring device 140.

Electric power is supplied from the operation device 7 to the blower device 8 through the electric power distribution line 180 and a transmission/reception interface 100. Then, the electric power is distributed from the DC input part 110 to the blower driver 150 which drives the blower 160. The blower driver 150 is controlled by the blower device control unit 120.

The blower device control unit 120 includes a CPU, a RAM, a ROM and the like for performing control of the blower device 8. The central processing unit is referred to as the CPU. The CPU executes various programs thus realizing various functions. The RAM is used as a work area and a storage area for the CPU. The ROM stores an operating system and programs to be executed by the CPU. When only a simple control is required, the blower device control unit 120 may be formed of an FPGA (Field-programmable Gate Array). In the same manner, the control unit 30 may also be formed of an FPGA.

A flow rate and a pressure measured by the flow rate measuring device 130 and the pressure measuring device 140 may be compared with setting values for flow rate and pressure of pressurized air for CPAP acquired through the communication means 170 by the blower device control unit 120. In such a case, the blower device control unit 120 may adjust the blower driver 150 thus having a function of adjusting a pressure in the air tube 250 to a fixed pressure.

Pressurized air generated by compressing air using the blower 160 is supplied to a soundproofing device 230 connected to a breathing circuit connection port 200 through a flow passage 190. The soundproofing device 230 is equipped with a humidifier connection portion 285 through which the soundproofing device 230 is connected to the humidifier 15. A humidifying part 240 is disposed from a water storage part 210 to the inside of the air tube 250. Sound absorbing members 220 are disposed in the soundproofing device 230. The sound absorbing member 220 is made of a soundproofing material such as flexible polyurethane foam thus preventing noises and vibrations which the blower 160 generates from being introduced to the attachment part 4 through the air tube 250. The soundproofing device 230 and the humidifier 15 are described in detail with reference to FIG. 3. The soundproofing device may be omitted.

The soundproofing device 230 has an air-tube-side connection portion 275 connected to the air tube 250, a body-side connection portion 280 connected to the breathing circuit connection port 200, and the humidifier connection portion 285 through which the soundproofing device 230 is connected to the humidifier 15 (see FIG. 3). The sound absorbing members 220 are disposed between the air-tube-side connection portion 275 and the body-side connection portion 280. The soundproofing device 230 may be divided into two portions consisting of a portion for the air tube 250 side and a portion for the body-side connection portion 280 side.

The humidifier 15 is roughly formed of the water storage part 210 and the humidifying part 240. The humidifying part 240 is formed of a tube 235, and a large number of hollow fibers 245 connected to the tube 235.

Water 270 is stored in the water storage part 210, and the tube 235 forming a portion of the humidifying part 240 is inserted into the water 270. A check valve 247 is connected to the water storage part 210 so that a mechanism is provided where air can be injected into the water storage part 210 from the outside. The water storage part 210 is formed of an elastic member. When a pressure applied to the water 270 is lower than a pressure in the air tube 250, water does not easily evaporate through the hollow fibers 245. Accordingly, the water storage part 210 is formed of an elastic member so as to pressurize water such that a pressure higher than a pressure of pressurized air compressed by the blower 160 can be applied to the water 270 constantly during sleep.

Distal end portions of the hollow fibers 245 on the side opposite to the side where the hollow fibers 245 are connected to the tube 235 are closed. Accordingly, there is no possibility that the water 270 is brought into direct contact with pressurized air in the air tube 250. The hollow fiber 245 is desirably made of a porous material in which a large number of pores are formed, and the pores have a fine size allowing water molecules in the form of a gaseous vapor to pass therethrough, but not allowing water in the form of liquid to pass therethrough.

Next, the manner of operation of the humidifier 15 is described.

The water 270 to which a pressure is applied in the water storage part 210 is introduced into the tube 235. Next, the tube 235 is connected to the inside of the soundproofing device 230 through the humidifier connection portion 285 so that the water 270 is introduced to the hollow fibers 245. Then, moisture evaporates through the fine pores formed in surfaces of the hollow fibers 245 in the air tube 250 so that pressurized air is humidified. Compared to the above-mentioned humidifier which is generally used, the humidifier in this embodiment requires no heating part so that a large-capacity power source is unnecessary. Accordingly, the lightweight and compact humidifier can be prepared, and the humidifier does not generate a sound. There is no possibility that the water 270 is brought into direct contact with pressurized air and hence, it is sufficient to use tap water for the water 270. That is, it is unnecessary to use purified water, which is cost-effective. The humidifying part 240 may be configured to be exchangeable.

As another method for forming the humidifying part 240, a method may be considered where a member which causes capillary action is enclosed in the air tube 250 instead of the hollow fibers. To be more specific, a non-woven fabric or the like can be enclosed. In this case, the water storage part 210 may not be formed of an elastic member. This is because even when water is not pressurized by the water storage part 210, by immersing the member of the humidifying part 240 which causes capillary action into water in the water storage part 210, moisture is transferred due to capillary action. Also in this case, the humidifying part 240 in the air tube 250 is desirably made of a porous material in which a large number of pores are formed, and the pores have a fine size not allowing water in the form of liquid to pass therethrough, but allowing water molecules in the form of a gaseous vapor to pass therethrough.

An air tube 290 connected to the soundproofing device 230 is terminally joined to the attachment part 4 (not shown in the drawing) so that pressurized air is supplied to the airway through the nose portion or the mouth portion. In such a case, it is desirable to set the length of the air tube 250 to 30 cm or more and 1 m or less so as to reduce a weight of the air tube 250 per se. When the length of the air tube 250 is set to 1 m or less, the influence of the own weight of the air tube 250 on the attachment part 4 is largely reduced and, further, favorable portability can be acquired. Further, when the length of the air tube 250 is set to 30 cm or more, a required length of hollow fibers can be ensured in the humidifying part 240 disposed in the air tube 250 so that pressurized air can be humidified to an approximately 70% which is an optimum moisture. Moreover, it is possible to reduce the feeling of constraint affecting the head which is caused by the air tube per se due to an extremely short length of the air tube 250.

The attachment part may be of a Nasal-type which covers the entire nose, or of a Prong-type which is inserted into the nostrils. Alternatively, the attachment part may be of a Full-Face-type which covers both the nose portion and the mouth portion. By forming the operation device 7, the blower device 8, the humidifier 15 and the like as described above, it is possible to realize the respiratory assistance device 1 having a small size and light weight at low cost.

The blower device 8 may be provided with a heating part 195 so as to control pressurized air to a fixed temperature. The heating part 195 may be provided so as to prevent the patient from being disturbed from sleep by cold air. In such a case, means for measuring a temperature of pressurized air may be disposed on the downstream side of the heating part 195 in the flow passage 190 so as to control heating of the heating part 195 and, as a result, pressurized air in the air tube 250 may be increased to approximately 37 degrees Celsius which is close to a body temperature, for example. The heating part 195 may be formed of a normal resistance heating heater which uses a nichrome wire or the like, and a heating may be controlled by the blower device control unit 120. The heating part 195 may be provided to the air tube 250.

The respiratory assistance device of the present invention is not limited to the above-mentioned embodiment, and it is needless to say that various changes may be applied to the respiratory assistance device without departing from the gist of the present invention. For example, the flow rate measuring device 130 and the pressure measuring device 140 may be disposed in the air tube 250 or in the soundproofing device 230.

Next, the manner of operation in the first embodiment having the above-mentioned configuration is described with reference to FIG. 4, FIG. 5, and FIG. 6. FIG. 4 is a conceptual view showing a usage mode of the respiratory assistance device 1 according to the first embodiment of the present invention. First, according to a setting value prescribed by a doctor, a pressure necessary for Auto CPAP respiratory therapy is set in the respiratory assistance device 1. At this time of operation, setting values are desirably inputted from the memory device such as an SD card through the interface 60 to the memory device (see FIG. 2). Next, the control unit 30 of the operation device 7 controls the entire respiratory assistance device 1. Further, the blower device control unit 120 controls the blower driver 150 such that flow rate and pressure of pressurized air from the blower 160 disposed in the blower device 8 are stabilized at the above-described setting values. At this time of operation, flow rate and pressure of pressurized air in the air tube 250 are measured in real time by the flow rate measuring device 130 and the pressure measuring device 140, and the blower device control unit 120 performs a feedback control such that the flow rate and the pressure are stabilized at the above-described setting values. A natural evaporation type humidifier is connected to the soundproofing device 230 disposed in a passage toward the air tube 250 so that pressurized air is sufficiently humidified. The air tube 250 is connected to the attachment part 4, and the respiratory assistance device 1 of this embodiment performs Auto CPAP therapy constantly during sleep time. According to this embodiment, the air tube 250 has a short length thus giving the air tube 250 a small size and light weight even in combination with the blower device 8 and the humidifier 15. Accordingly, the degree of freedom of the attachment part which is connected to the air tube 250 is increased so that it is possible to acquire an advantageous effect that the patient can easily roll over thus contributing to the enhancement of QOL of the patient. The above-mentioned advantageous effects are specifically described with reference to FIG. 5.

FIG. 5(a), FIG. 5(b), and FIG. 5(c) are explanatory views of a patient attachment the respiratory assistance device 1 according to the first embodiment of the present invention as viewed in the direction from the top of the head. FIG. 5(a) shows a case where a patient is lying on his back. In this case, the attachment part 4 is attached to the patient so as to be directed upward in the vertical direction so that the air tube 3 extends toward the blower device 8 (blower device casing 400). Assume that the patient tries to roll over such that, as shown in FIG. 5(b), the body is rolled in the counterclockwise direction as viewed in the direction from the top of the head. In the conventional respiratory assistance device 1 shown in FIG. 10, the degree of freedom of the attachment part is increased by increasing the length of the air tube 3. However, in such a case, the air tube 3 has a weight to some extent thus preventing the head from turning. On the other hand, according to the respiratory assistance device 1 of the first embodiment of the present invention, the blower device 8 has a light weight and hence, a patient can naturally pull the air tube 3, to which the blower device 8 is connected, by the force of rolling over. That is, the blower device 8 can be displaced to a position B closer to the body from an original position A. Accordingly, unlike the conventional respiratory assistance device 1 shown in FIG. 8 which requires an increase in length of the air tube 3 so as to increase the degree of freedom of the attachment part, the degree of freedom of the attachment part can be increased with the air tube 3 having a short length. To the contrary, assume that the patient tries to roll over such that, as shown in FIG. 5(c), the body is rolled in the clockwise direction as viewed in the direction from the top of the head. In this case, the blower device 8 is pushed by the air tube 3. When the air tube 3 is made of a material having a high modulus of elasticity, it may be considered that the air tube 3 connected to the attachment part 4 attached to the face prevents the patient from rolling over. However, in the respiratory assistance device 1 according to the first embodiment of the present invention, the blower device 8 has a light weight and hence, the blower device 8 can be naturally pushed by the force of rolling over. That is, as shown in FIG. 5(c), the blower device 8 can be easily displaced to a position C farther away from the body from the original position A and hence, the patient can naturally roll over. As described above, according to the respiratory assistance device 1 of the first embodiment of the present invention, QOL of a patient is enhanced.

As shown in FIG. 6, in operating the operation device 7 (operation device casing 300), a patient can operate the operation device 7 just by taking the operation device 7 in hand without moving the blower device 8 (blower device casing 400). The operation device 7 does not incorporate the blower 160 and hence, compared to a conventional body device (see FIG. 10) where an operation device and a blower device are formed into an integral body, the operation device 7 can be formed with a lighter weight and a more compact size and hence, it is possible to acquire an advantageous effect that a burden on a user during operation is small.

Next, the configuration of a respiratory assistance device 1 according to a second embodiment of the present invention is described with reference to FIG. 7 and FIG. 8.

FIG. 7 is a detailed block diagram of the respiratory assistance device 1 according to the second embodiment of the present invention. First, the configuration of an operation device 7 is described. The operation device 7 is accommodated in an operation device casing 300 independent from a blower device 8. The operation device 7 is formed of a power source unit 10, a DC power circuit 20, a control unit 30, an operation interface 50 and the like.

Next, the blower device 8 is described. The blower device 8 is accommodated in a blower device casing 400 independent from the operation device casing 300. The blower device 8 includes a display part 40, a blower device control unit 120, a blower driver 150, a blower 160, a flow rate measuring device 130, a pressure measuring device 140 and the like. The blower 160 is controlled based on information acquired through communication means 170 so that pressurized air having flow rate and pressure which conform to setting values is generated. A point which makes this embodiment different from the first embodiment lies in that the display part 40 is included in the blower device 8 disposed close to hand. A patient can easily see real time measured values displayed on the display part 40 in a lying posture and hence, it is possible to acquire an advantageous effect that the patient can receive Auto CPAP respiratory therapy with the feeling of comfort (see FIG. 8). The blower device 8 may further include a mechanism which can make simple adjustment to flow rate and pressure.

The configuration of a respiratory assistance device 1 according to a third embodiment of the present invention is described with reference to FIG. 9.

FIG. 9 is a detailed block diagram of the respiratory assistance device 1 according to the third embodiment of the present invention. In the third embodiment of the present invention, the respiratory assistance device 1 includes three casings consisting of a power source circuit casing 500, an operation device casing 300, and a blower device casing 400. The power source circuit casing 500 and the operation device casing 300 are connected to each other via a DC power source line 75. The operation device casing 300 and the blower device casing 400 are connected to each other via communication means 170 and an electric power distribution line 180. The power source circuit casing 500 includes an AC inlet 9, a power source unit 10, a DC output part 70 and the like. The power source unit 10 including an AC/DC converter which is relatively heavy is independent from the operation device casing 300 and hence, the operation device casing 300 can be further reduced in size and weight whereby it is possible to acquire an advantageous effect that the operation device casing 300 can be easily disposed on a bed. The power source unit 10 includes parts which generate an electromagnetic noise such as a switching regulator. Accordingly, by disposing the power source circuit casing 500 separately so as to isolate the control unit 30 from negative impact caused by noises, it is also possible to acquire an advantageous effect of providing a safer respiratory assistance device 1. In the third embodiment, an example has described where a display part 40 is included in the operation device casing 300. However, it may be also considered that the display part 40 is included in the blower device casing 400.

In the above-mentioned embodiments, the respiratory assistance devices preferably used for Auto CPAP respiratory therapy are exemplified. However, it is needless to say that the present invention is not limited to the above, and the present invention is also applicable to a respiratory assistance device for other purposes.

The invention claimed is:

1. A respiratory assistance device used during sleep as a continuous positive airway pressure therapy for a patient with sleep apnea syndrome comprising:
    a blower device including a blower configured to generate pressurized air;
    an operation device including an operation interface configured to control the blower; wireless or wired communication line configured to connect the blower device and the operation device to each other;
    an attachment part comprising a nasal-type attachment which is configured to cover a nose of the patient, a prong-type attachment which is configured to be inserted into the patient's nostrils, or a full-face-type attachment which is configured to cover both the nose and a mouth of the patient, the attachment part being configured to be attached to a head of the patient so as to supply the pressurized air to an airway of the patient; and
    an air tube through which the pressurized air is introduced into the attachment part from the blower device,
    wherein the blower device is accommodated in a blower device casing, and the operation device is accommodated in an operation device casing separate from the blower device casing;
    and further comprising:
    a power source unit accommodated in the operation device casing, and configured to supply electric power to the blower and the operation interface;
    an electric power distribution line configured to distribute the electric power from the power source unit to the blower device casing; and
    a flow rate measuring device and a pressure measuring device in the blower device casing, and configured to measure a flow rare and a pressure of the pressurized air in real time, respectively;
    wherein a length of the electric power distribution line is set to 50 cm or more and a length of the air tube is set to 30 cm or more, and the blower device casing and the operation device casing are not secured to the patient, so that the blower device casing and the operation device casing do not interfere with the patient when the patient rolls over during sleep;
    the blower device includes a blower device control unit and a blower driver controlled by the blower device control unit;
    the operation device includes an operation control unit which compares the flow rate and the pressure of the pressurized air and setting conditions inputted from the operation device, and transmits a control command to the blower device control unit; and
    the blower device control unit controls the blower driver based on the control command from the operation control unit.

2. The respiratory assistance device according to claim 1, wherein the control command is transmitted to the operation control unit through the wireless or wired communication line.

3. The respiratory assistance device according to claim 1, wherein the length of the air tube is set to 1 m or less.

4. The respiratory assistance device according to claim 1, further comprising a humidifier configured to provide moisture to the pressurized air.

5. The respiratory assistance device according to claim 4, wherein the humidifier includes: a water storage part configured to contain water for humidification; and a humidifying part disposed in the air tube, and configured to humidify the pressurized air with water in the water storage part.

6. The respiratory assistance device according to claim 5, wherein the humidifier further includes a pressure applying part configured to pressurize water in the water storage part.

7. The respiratory assistance device according to claim 4, further comprising a soundproofing device disposed at an intermediate portion of a flow passage for the pressurized air, and configured to absorb sound of the blower.

8. The respiratory assistance device according to claim 7, wherein the soundproofing device includes: a humidifier connection portion connected to the humidifier; a body-side connection portion connected to a breathing circuit connection port; an air-tube-side connection portion connected to the air tube; and a sound absorbing member disposed between the body-side connection portion and the air-tube-side connection portion.

9. The respiratory assistance device according to claim 1, further comprising a heating part capable of heating the pressurized air to a predetermined temperature.

* * * * *